United States Patent [19]

Riester

[11] 4,366,811

[45] Jan. 4, 1983

[54] OTOSCOPE WITH EJECTOR MECHANISM

[75] Inventor: Karlheinz Riester, Jungingen, Fed. Rep. of Germany

[73] Assignee: Rudolf Riester GmbH & Co., Jungingen, Fed. Rep. of Germany

[21] Appl. No.: 243,853

[22] Filed: Mar. 16, 1981

[30] Foreign Application Priority Data

Mar. 14, 1980 [DE] Fed. Rep. of Germany ....... 3009876

[51] Int. Cl.³ ........................... A61B 1/22; A61B 1/06
[52] U.S. Cl. ........................................... 128/9; 128/6; 128/4
[58] Field of Search ............................. 128/4, 6, 9, 11

[56] References Cited

U.S. PATENT DOCUMENTS 2,797,684  7/1957  Moore ..................................... 128/9
3,812,847  5/1974  Moore et al. ........................... 128/9
3,840,004  10/1974  Heine ..................................... 128/9
3,878,836  4/1975  Twentier ................................ 128/9
3,949,740  4/1976  Twentier ................................ 128/9

Primary Examiner—Kyle L. Howell
Assistant Examiner—Nancy A. B. Swisher
Attorney, Agent, or Firm—Holman & Stern

[57] ABSTRACT

This invention is an improvement in otoscopes for ear examinations and the like wherein disposable ear funnels are ejected from the instrument remotely thus avoiding contact by the examiner after use. An ejector is provided in the head portion of the housing of the instrument between the magnifying eyepiece and the ear funnel. The eyepiece is movably mounted so that it can be depressed to engage and move the ejector to thereby eject the ear funnel.

11 Claims, 4 Drawing Figures form 4,366,811

OTOSCOPE WITH EJECTOR MECHANISM

BRIEF SUMMARY OF THE INVENTION

The invention concerns an otoscope with a housing having an examination opening for examining a lighted field, which opening is surrounded by at least one funnel shaped piece the axis of which is close to the observation line or coincides with it, or is at least approximately parallel to it, and having a disposable funnel outer shaped piece removably mounted on the front end of the housing.

Medical diagnostic instruments such as ophthalmoscopes, otoscopes and the like frequently have a part which comes in contact with the patient. In an otoscope this part is an ear funnel i.e., ear speculum, which is inserted into the patient's ear.

It is already known to connect this ear funnel to the housing of the otoscope in replaceable fashion. This makes it possible to remove the ear funnel from the otoscope after each use and replace it with a new ear funnel for the next patient. Conversion to disposable ear funnels is thus possible.

This arrangement is helpful. However it is a disadvantage that the ear funnel must be removed by hand from the diagnosing instrument by the attending physician or his assistant. Contact thus must be made with the outer surface of the ear funnel, which may have been dirtied or contaminated with infectious material by contact with the patient. This is unhygienic and necessitates additional expense for cleaning, or the use of additional implements for removing the ear funnel.

The underlying objective of the invention is thus to provide a medical diagnosing instrument, such as an otoscope or the like, with an integrated mechanism which obviates the necessity to touch the funnel in removing it from the instrument.

This problem is solved according to the invention by providing in the housing a movable ejector which engages on one end the removable ear funnel and on the other end an ejection actuator for use in ejecting the removable ear funnel.

After an ear examination has been completed one need only press the ejection actuator, which motion is converted into an ejection stroke of the ejector, which thereby separates the ear funnel from the instrument. This process may be carried out above a waste receptacle or the like into which the used ear funnel falls after separating from the instrument. The instrument is quickly made ready for use again by mounting a new ear funnel. In this way one has a device which for the first time completely exploits the advantages of a disposable ear funnel in the manipulation of the instrument.

Advantageously, the magnifying eyepiece of the otoscope is used as the ejection actuator by being pivotably mounted to the housing at one of its edges, and having a swing-actuating handle at the opposite edge. It is useful for the magnifying eyepiece to have a ridge or similar projection on its side facing the housing, whereby a projection at the rear end of the ejector, which projection projects beyond the housing or into a recess in the housing provided for the magnifying eyepiece, lies in the path of motion of the ridge on the magnifying eyepiece. This gives the ejector a very simple construction, since the ejection actuator is fashioned from an already existing part of the instrument. The only additional part which must be provided is the ejector itself.

Advantageously the ejector is in the form of an ejector plate, made from steel sheet, plastic, or the like, capable of providing the necessary rigidity. This rigidity may be ensured extremely simply with multiple bends produced by bending or stamping. This type of plate is easy to manufacture and to adapt to fit within the free space inside the instrument. A piece of even low inherent rigidity will be sufficiently rigidified by the bends and curves to directly convert the stroke of the ejection actuator into an ejection stroke against the disposable ear funnel. For this it suffices for the front end of the ejector plate to directly engage the rear end of the disposable ear funnel. This engagement is effected in a suitable fashion for the funnel to be reliably ejected when the ejector is actuated. In this connection it may be desirable for the ejector plate to engage the ear funnel at more than one point, preferably at two nearly diametrically opposite points. However, depending on the means of releasable attachment of the ejector to the housing, and depending on space demands, it is often sufficient for the ejector to engage the ear funnel only at a single point or over a short distance on the rear perimeter of the ear funnel, or if necessary or desirable even at some distance off-axis. If desirable an ejector in plate form may have an opening in its middle through which any pieces may pass which may need to run along the axis of the housing grip from the housing grip to the housing head.

Thus one has, very simply and without effecting instrument performance, provided a device by which a disposable ear funnel may be separated from the otoscope and discarded without touching the ear funnel itself, but merely by pressing on the magnifying eyepiece. This concept is also readily applicable to other medical diagnostic instruments of related types.

BRIEF DESCRIPTION OF THE SEVERAL VIEWS OF THE DRAWING

A preferred embodiment of this invention will now be described with reference to the attached drawings wherein.

DETAILED DESCRIPTION

Figure 1:
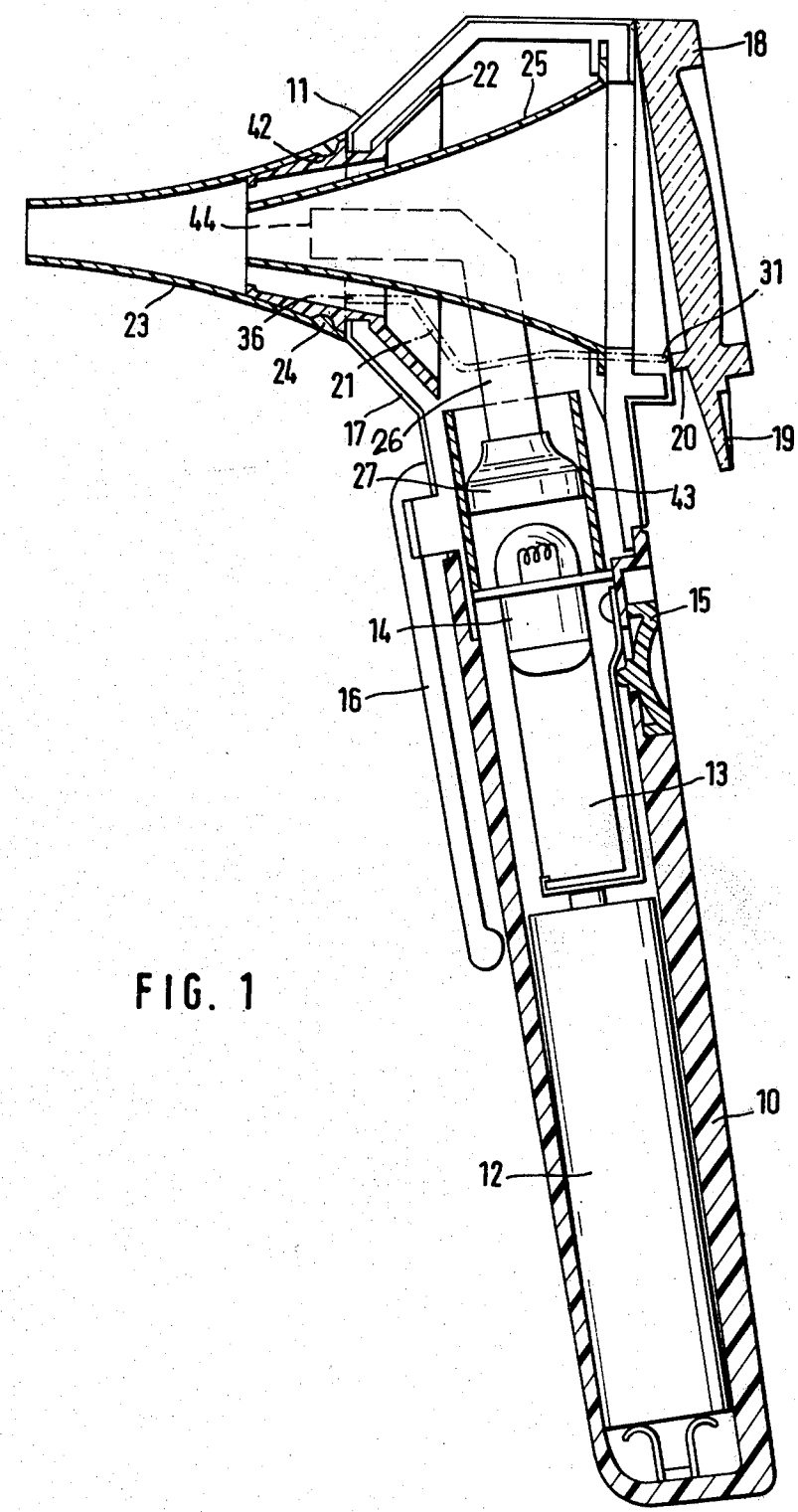
FIG. 1 is a simplified cross sectional view of the otoscope of this invention with an ejector.

FIG. 1 indicates the overall construction of the otoscope. There is a housing grip 10 and a housing head 11. The latter may be in two parts, with the plane of division being the central longitudinal plane of the instrument. Housing grip 10 contains a battery 12, a lamp holder 13, an illuminating lamp 14, and a switch 15 for turning on lamp 14, with said switch being appropriately located and shaped from a bioengineering standpoint. In particular, this switch is on the side of grip 10 facing the user. On the opposite side there is a clip 16 for securing the instrument to the physician's coat. Housing grip 10 may advantageously be made of plastic.

Housing head 11 is attached to housing grip 10 by means of a latch connector or the like, not shown in FIG. 1. Housing head 11 is in two halves 17, the right one of which is visible as viewed from the right. The housing head has at its rear a viewing opening which is covered by a magnifying eyepiece 18. The latter is swingably attached at its upper edge to the housing head 11. It is practically square in overall shape, with rounded corners. At its lower edge it has an actuation grip 19 by which the magnifying eyepiece can be pressed into an opening on the rear side of housing head 11. This grip may be knurled. There is also a ridge 20 on the housing head side of eyepiece 18 near actuating grip 19. This ridge moves up against the rear edge 31 of a bent ejector plate 21 which extends to its front end 36 by passing through the interior space of the instrument.

At the front end of housing head 11 the head halves 17 engage and hold a funnel holder 22, of the configuration shown. Holder 22 at its rear end part has a truncated cone configuration which lies against a mating surface on the inner wall of the head halves 17. The front part of holder 22 projects beyond head halves 17 in a concave cone shape which tapers downwardly toward the front, forming the receiving piece for the outer conical member 23 which may be disposable. Cone holder 22 has a groove 42 in its base just in front of the front end of the head halves 17 which provides for the releasable fastening of outer cone 23 to cone holder 22. Correspondingly, outer cone 23 has an inward projection 24 for engaging said groove. Outer cone 23 can thus be pushed in simple fashion over cone holder 22 where it is releasably fastened with the aid of projection 24 and the groove 42.

The front end 36 of ejector plate 21 engages the rear end of outer cone 23. An inner cone 25 covers the parts located in the peripheral region inside the head halves 17 and the cone holder 22 so that these cannot be sighted through the magnifying eyepiece 18, and it defines a good observation path through the diagnosing instrument, with a definite observation direction.

Light-conducting rods 26 are located between inner cone 25 and outer cone 23 and between inner cone 25 and the inner surface of cone holder 22. Where these rods 26 are hidden by inner cone 25 as seen in FIG. 1 they are shown in dashed lines. The light-receiving end surfaces of light-conducting rods 26 are positioned in a light-receiving holder 27 directly in front of illuminating lamp 14. If desired, a support 43 in the light-emitting direction of illuminating lamp 14 is provided, for a condenser or the like, which concentrates the light emitted from illuminating lamp 14 onto the light-receiving end surface of light-conducting rods 26.

Starting at the light-receiving holder 27 the light-conducting rods pass first integrally together and then split or fork apart to pass between the outside inner funnel 25 and the inside of head halves 17. This makes it necessary for ejector plate 21 (shown in dashed lines in FIG. 1) to have an opening 33 through which the light-conducting rods pass without hindering its movement. Alternatively, the light-conducting rods may be configured so as to lie outside the outer edges of ejector plate 21. The light-conducting rods are arranged at their front ends 44 so as to be held between the inner walls of funnel holder 22 and the outer walls of inner funnel 25.

In the following, further details concerning the construction and functioning of the ejector plate 21 will be given.

Figure 2:
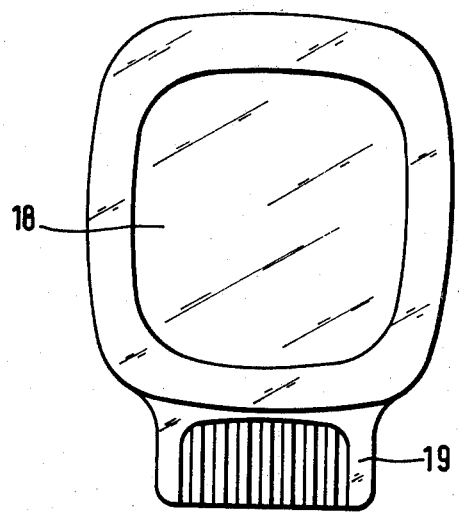
FIG. 2 is an elevation view of the magnifying eyepiece of the otoscope of FIG. 1, with the view magnified 2:1.

FIG. 2 is an elevation view of magnifying eyepiece 18 with its actuating grip 19 at the bottom. This figure gives a better picture of the design of the eyepiece than does the side view of FIG. 1. Notably, it is seen that actuating grip 19 is quite wide, and like switch 15 it is appropriately positioned from a bioengineering standpoint within reach of the physician's thumb when his hand grips the otoscope on its housing grip 10. As a consequence of the nearly square shape of magnifying eyepiece 18 there is adequate surface area available on the housing side of eyepiece 18 to effect actuation of even a complex shaped ejector plate. In the embodiment shown, the actuating surface is in the form of a ridge 20 which projects outwardly on the housing side of eyepiece 18 and serves to guide eyepiece 18 in motion on the housing head 11 and to actuate the ejector plate 21 by engagement with the rear edge 31 thereof.

Figure 3:
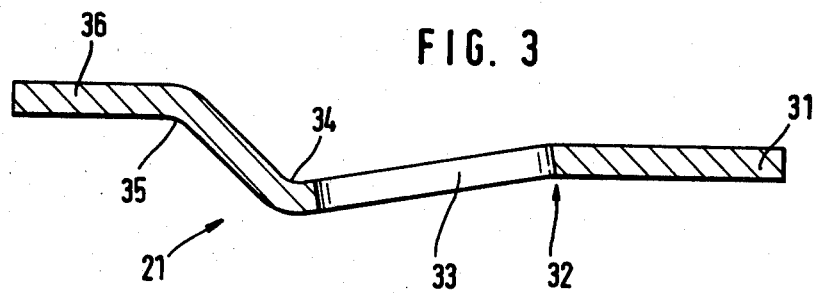
FIG. 3 is a longitudinal cross sectional view of the ejector plate in the same cross section plane as FIG. 1 with the view magnified 5:1.
Figure 4:
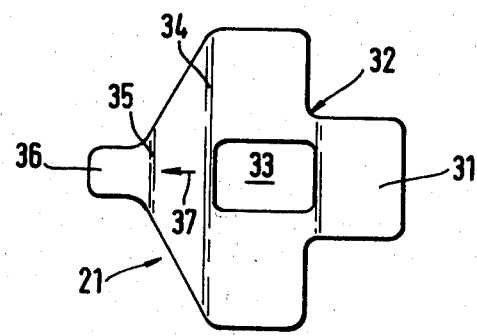
FIG. 4 is a top view of the ejector plate of FIG. 3, with the view magnified 2:1.

FIG. 3 is a magnified cross sectional view and FIG. 4 is a plan view of a possible construction for the ejector plate. The cutting plane of the cross section of FIG. 3 is the longitudinal center plane of the instrument. The rear end of ejector plate 21 forms a projection 31 which lies in the path of movement of ridge 20, and this projection establishes the contact between magnifying eyepiece 18 and ejector plate 21. The ejector plate extends first in a plane approximately parallel to the observation direction and then bends downward at line 32 into a plane which is perpendicular to the longitudinal axis of housing grip 10. In this region ejector plate 21 has an opening 33 through which the light-conducting rods 26 pass. The length of opening 33, in the ejection or observation direction, exceeds its breadth (transverse thereto), in order to allow the necessary movement for the ejection stroke. Farther forward beyond bend line 32 and opening 33 there is a bend section 34 in which ejector plate 21 is bent steeply upwardly. The front end section 36 lies beyond a third bend section 35 and runs approximately parallel to the observation direction, or ejection direction. Thus, front end section 36 of ejector plate 21 lies in a plane substantially parallel to that of projection 31 but higher than the latter. Front end section 36 contacts the rear end of outer funnel 23 which, as a disposable ear funnel, is to be discarded after the use of the diagnosing instrument.

FIG. 4 shows the shape of ejection plate 21, with a number of outer edges running parallel to the observation (or ejection) direction (arrow 37), which edges bound projection 31 at the breadth of ridge 20 on magnifying eyepiece 18, further bound a wider middle section, and finally bound front end section 36. The parallel side edges of projection 31 and front end section 36 can function in guiding ejector plate 21 during the ejection motion.

The ejector operates as follows: when the physician presses on the actuating grip 19 of magnifying eyepiece 18, ejection plate 21 is translated in the directon of arrow 37 and thereby releases projection 24 on outer funnel 23 from groove 42 on funnel holder 22, whereby the disposable ear funnel is ejected. If a new ear funnel is now mounted by pushing it over funnel holder 22, the ejector plate 21 and the eyepiece 18 are returned to their normal positions. A catch or locking device may also be provided to hold eyepiece 18 in its normal position. The normal position of magnifying eyepiece 18 should be such as to allow the observation of the examination field through the entire observation opening of the instrument.

What I claim is:

1. An otoscope comprising having a housing, an observation opening at the first end of said housing for examining a lighted examination field, a magnifying eyepiece at the rear end of said housing with at least one funnel shaped piece in said housing surrounding said opening, the axis of which is substantially parallel to the observation line, and a funnel shaped piece removably mounted ear funnel on the front end of the housing, an ejector movably mounted within said housing with an ejection actuator means mounted on said housing, said ejector engaging at one side said removable ear funnel and at the other side of said ejection actuator means so that operation ejection actuator means moves said ejector to eject said removable ear funnel.

2. The device as claimed in claim 1 wherein said magnifying eyepiece is movably mounted on said housing and said ejection actuator means is said magnifying eyepiece.

3. The device as claimed in claim 2 wherein said magnifying eyepiece is pivotally mounted on one edge to said housing, and has a grip piece at the opposite edge which when depressed causes said ejector to eject the ear funnel.

4. The device as claimed in claim 2 or 3, and further comprising a protruding ridge on the side of said magnifying eyepiece facing the housing, a projection at the rear end of the ejector projecting into the path of motion of said ridge on the magnifying eyepiece so that depressing said eyepiece toward said housing engages said ridge with said projection and thereby moves said ejector to eject said ear funnel.

5. The device as claimed in claim 1 wherein said ejector is in the form of a plate.

6. The device as claimed in claim 5, wherein said ejection plate has multiple bends produced by stamping to facilitate operation within said housing.

7. The device as claimed in claim 6 wherein said one side of said ejector which engages said ear funnel is the front end of the ejection plate and engages the rear end of said ear funnel, and said ejector plate is mounted so that its said front end is movable in the ejection direction by said actuator.

8. The device as claimed in claim 7 wherein two funnels are provided in the housing comprising, an outer funnel for supporting said ear funnel therein in use and an inner funnel extending substantially coaxially through said outer funnel in spaced relationship therewith, and further comprising means to releasably retain said ear funnel on said outer funnel, said ejection plate being disposed partly in the space between said two funnels and partly between said inner funnel and the inner wall of said housing.

9. The device as claimed in claim 8 and further comprising an opening in the substantially middle portion of said ejector plate, and a light-conducting means in said housing passing through said opening and positioned between said inner and outer funnels and between said inner funnel and the housing wall.

10. The device as claimed in claim 9, and further comprising a spring means to resiliently urge said ejector and ejection actuator toward their normal non-ejecting positions.

11. The device as claimed in claim 9 and further comprising a latch means to releasably retain said actuator in its normal non-ejecting position.

* * * * *